US011898309B2

(12) United States Patent
Wennberg et al.

(10) Patent No.: US 11,898,309 B2
(45) Date of Patent: Feb. 13, 2024

(54) METHOD AND A SYSTEM FOR OBTAINING METHANOL FROM FOUL CONDENSATE OF A PULPING PROCESS

(71) Applicant: VALMET AB, Sundsvall (SE)

(72) Inventors: Olle Wennberg, Västra Frölunda (SE); David Blomberg Saitton, Domsjö (SE); Thomas Nordlander, Örnsköldsvik (SE)

(73) Assignee: VALMET AB, Sundsvall (SE)

( * ) Notice: Subject to any disclaimer, the term of this patent is extended or adjusted under 35 U.S.C. 154(b) by 603 days.

(21) Appl. No.: 16/973,196

(22) PCT Filed: Jun. 11, 2019

(86) PCT No.: PCT/SE2019/050542
§ 371 (c)(1),
(2) Date: Dec. 8, 2020

(87) PCT Pub. No.: WO2019/240654
PCT Pub. Date: Dec. 19, 2019

(65) Prior Publication Data
US 2021/0087745 A1    Mar. 25, 2021

(30) Foreign Application Priority Data

Jun. 11, 2018  (SE) .................... 1850706-1

(51) Int. Cl.
*D21C 11/00* (2006.01)
*C07C 29/80* (2006.01)
(Continued)

(52) U.S. Cl.
CPC .......... *D21C 11/0007* (2013.01); *C07C 29/80* (2013.01); *D21C 11/06* (2013.01); *C07C 31/04* (2013.01)

(58) Field of Classification Search
CPC ..... D21C 11/0007; D21C 11/06; C07C 29/80; C07C 31/04
See application file for complete search history.

(56) References Cited

U.S. PATENT DOCUMENTS

| 2,605,276 A | 7/1952 | Bruner et al. |
| 4,915,784 A * | 4/1990 | Reynolds ............... B01D 5/009 585/803 |

(Continued)

FOREIGN PATENT DOCUMENTS

| CA | 1088957 A | 11/1980 | |
| CN | 101918305 A * | 12/2010 | ......... C01B 13/0248 |

(Continued)

OTHER PUBLICATIONS

Valmet, Methanol-Waste Byproduct to Valuable Fuel, Nov. 20, 2018, Technical Paper Series (Year: 2018).*

(Continued)

*Primary Examiner* — Anthony Calandra
(74) *Attorney, Agent, or Firm* — Foley & Lardner LLP (57) ABSTRACT

Embodiments herein relate to a system (200; 300; 400; 500) for obtaining methanol from foul condensate (101) of a pulping process. The system (200; 300; 400; 500) comprises a primary stripper (102) arranged to strip the foul condensate (101) from pollutants, whereby a first methanol-containing condensate is obtained from the polluted stripper off gases (SOGs). The system (200; 300; 400; 500) also comprises a first acidification unit (202) arranged to acidify the first methanol-containing condensate. Further, the system (200; 300; 400; 500) comprises a secondary stripper (204) arranged to strip the acidified first methanol-containing condensate from pollutants to obtain a second methanol-containing condensate, and a distillation column (107) arranged to distil the second methanol-containing condensate from the secondary stripper (204) so as to obtain (Continued)

methanol. Embodiments herein also relate to a method performed in a system (200; 300; 400; 500) for obtaining methanol from foul condensate (101) of a pulping process.

11 Claims, 6 Drawing Sheets

(51) Int. Cl.
  *D21C 11/06* (2006.01)
  *C07C 31/04* (2006.01)

(56) References Cited

U.S. PATENT DOCUMENTS

| | | | |
|---|---|---|---|
| 6,217,711 | B1 | 4/2001 | Ryham et al. |
| 6,261,412 | B1 | 7/2001 | Ryham |
| 8,440,159 | B2 * | 5/2013 | Brucher ............... D21C 11/00 423/396 |
| 2011/0306807 | A1 | 12/2011 | Der et al. |
| 2016/0122267 | A1 | 5/2016 | Jemaa et al. |
| 2016/0237011 | A1 * | 8/2016 | Warnqvist ............... C07C 29/88 |

FOREIGN PATENT DOCUMENTS

| | | |
|---|---|---|
| CN | 104492112 A | 4/2015 |
| CN | 105324357 A | 2/2016 |
| WO | WO-96/23566 A1 | 8/1996 |
| WO | WO-00/01879 A1 | 1/2000 |
| WO | WO 2009/070110 A1 | 6/2009 |
| WO | WO 2010/091492 A1 | 8/2010 |
| WO | WO 2014/201555 A1 | 12/2014 |
| WO | WO 2015/053704 A1 | 4/2015 |

OTHER PUBLICATIONS

Valmet, Expansion of Chemical Recovery Capacity at Sodra Cell Varo Mill, Jul. 1, 2017, Technical Paper Series (Year: 2017).*
Wennberg et al., Purification of SOG—An Industrial Demonstration, 2017, ICRC (International Chemical Recovery Conference) (Year: 2017).*
Supplementary European Search Report, dated Dec. 21, 2021, 3 pages.
Ben Lin, The Basics of Foul Condensate Stripping, 2008, pp. 16 pages, retrieved from the internet: http://www.ahlundberg.com/wp/wp-content/uploads/2017/04/AHL-The-Basics-of-foul-condensate-stripping.pdf.
Office Action issued in connection with Chinese Appl. No. 201980039337.4, dated Apr. 2, 2022.

* cited by examiner

METHOD AND A SYSTEM FOR OBTAINING METHANOL FROM FOUL CONDENSATE OF A PULPING PROCESS

TECHNICAL FIELD

Embodiments herein relate to obtaining purified methanol. And embodiments herein relate in particular to a method and a system for obtaining methanol from foul condensate of a pulping process.

BACKGROUND

In a kraft production process of cellulose, known as pulping, cellulose and black liquor are formed during the cooking stage. Methanol is also formed during the cooking stage. The methanol will dissolve into the black liquor and be separated together with the black liquor from the cellulose. The black liquor is then concentrated during an evaporation stage before finally being burned in a soda-recovery boiler. During the evaporation stage condensate streams are formed, which mainly consist of water. Parts of these condensate streams also comprise other compounds or substances, such as, methanol, Total Reduced Sulphur (TRS), etc. The methanol and the TRS may be enriched in a separate condensate stream to form a so-called foul condensate. The foul condensate may then be purified in a so-called stripper or stripper column. A stripper conventionally uses water vapour to remove substances or pollutants from a liquid stream, where the pollutants are removed together with the stripping gases. In this case, the stripping gases, also commonly referred to as stripper off gas (SOG), will, besides water vapour and other pollutants, also contain a considerable amount of methanol.

The SOG, having a water content of 50-75%, can be incinerated or upgraded in a distillation column, where the methanol is concentrated and separated from the major part of the water content of the SOG. The SOG as well as the upgraded methanol is highly polluted by primarily three (3) different substances or pollutants: nitrogenous compounds, mainly in the form of ammonium; sulphurous compounds, mainly in the form of TRS; and turpentine and/or other non-water-soluble hydrocarbons. It should be noted that turpentine is primarily present when using so-called softwood, such as, spruce or pine, during the pulping process, while using so called hardwood, such as, e.g. *eucalyptus*, more oil-related substances will be present instead, albeit in a lesser degree.

The SOG could also be condensed to form a methanol-containing condensate, which can be further treated and thereby further upgraded to a higher quality. Depending on the applications for usage of the methanol, there is a need to be able to provide an improved purification of methanol from foul condensate of a pulping process.

Figure 1:
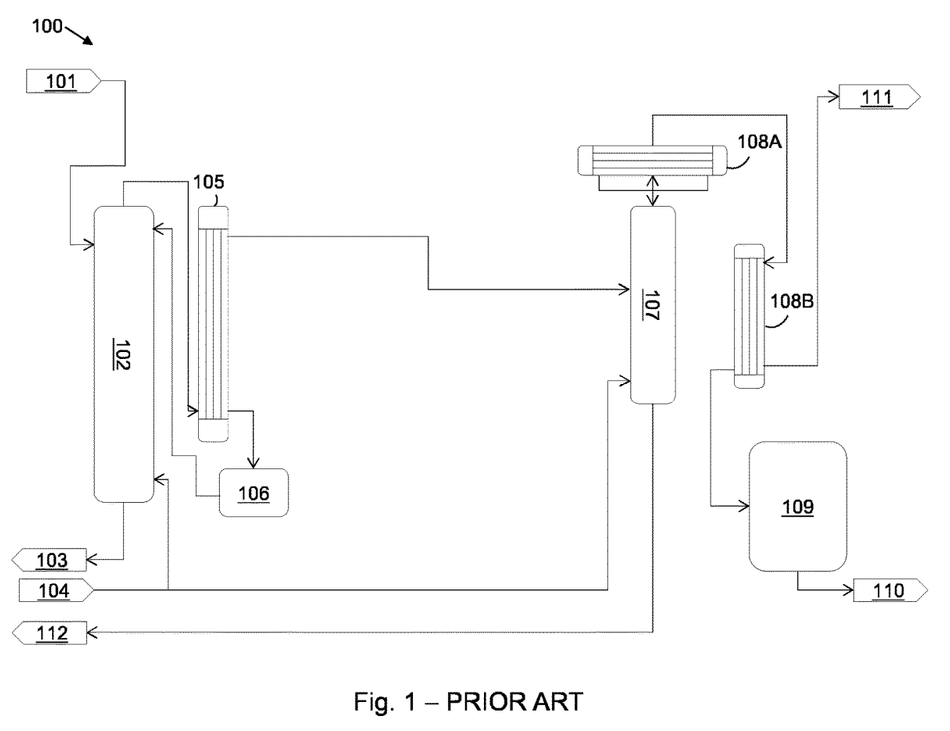
FIG. 1 is a schematic illustration depicting an example of a system for obtaining methanol from foul condensate of a pulping process according to prior art.

FIG. 1 depicts an example of a system 100 for obtaining methanol from foul condensate 101 of a pulping process according to prior art. The foul condensate 101 is feed into a primary stripper 102. In the primary stripper 102, water vapour 104 is used to remove volatile pollutants in the foul condensate. The methanol-containing water vapour being driven off may be referred to as stripping gases or stripper off gas (SOG). The remaining part of the foul condensate in the primary stripper 102 can be removed as a purified condensate 103 from the primary stripper 102. The SOGs are then transferred from the primary stripper 102 to a primary reflux condenser 105. In some cases, the primary reflux condenser 105 may be considered to form part of the primary stripper 102. The primary reflux condenser 105 will cool the SOGs. The major part of the SOGs will be condensed in the primary reflux condenser 105 and sent back to the primary stripper 102 in a so-called reflux stream, e.g. via a reflux tank 106, but the remaining part of SOGs, which is enriched with methanol, will be transferred into a distillation column 107. In the distillation column 107, water vapour 104 is normally provided to the bottom of the distillation column 107 to drive the distilling process. The distilled methanol from the distillation column 107 is then condensed via a distiller reflux condenser 108A and a distiller final condenser 108B. The distiller reflux condenser 108A is arranged to return the distiller reflux condensate to the distillation column 107 while a vapour stream is directed to the distiller final condenser 108B such that a methanol rich condensate from the distiller final condenser 108B is collected in a methanol tank 109 from which the methanol 110 can be extracted. It should also be noted that non-condensable gases 111, i.e. the non-condensable parts coming out of the distiller final condenser 108B, can be transferred away from the system 100. The major part of the water is found in the stream 112 coming out of the bottom the distillation column 107.

In order to further improve the process disclosed in FIG. 1 acid may be added in the process. Methods for purification of methanol from foul condensate are for example disclosed in CA 1,088,957 which discloses the acidifying of the SOGs from a foul condensate before entering a second stripper. However, even though the method in CA 1,088,957 discloses a method for producing methanol there is a desire for a product having higher purity. Also the publication "The basics of foul condensate stripping" (retrieved from http://www.ahlundberg.com/wp/wp-content/uploads/2017/04/AHL-The-Basics-of-foul-condensate-stripping.pdf, Ben Lin et al, 2008) discloses the use of acidifying in order to improve the purification of methanol from foul condensate. An essentially identical process is disclosed also in WO 2010/091492. However, the method disclosed in the publication by Ben Lin et al. and WO 2010/091492 also needs to be improved in order to provide a more pure methanol product.

SUMMARY

An object of the invention is to improve the purification of methanol from foul condensate of a pulping process.

According to a first aspect of embodiments herein, the objective is achieved by a system for obtaining methanol condensate from foul condensate of a pulping process. The system comprises a primary stripper arranged to strip the foul condensate from pollutants. The system also comprises at least a primary reflux condenser, which may be integrated with the primary stripper or be a separate unit, which partly condenses the vapour from the primary stripper and the condensate is returned to the primary stripper as so-called reflux condensate. The remaining vapour, often referred to as stripping gases or stripper off gases (SOGs), can be condensed in a SOG condenser, whereby a first methanol-containing condensate is obtained from the polluted SOGs of the primary stripper. If desired or needed, one or more additional SOG condensers can be used to obtain the methanol-containing condensate from the polluted SOGs. The SOGs from the primary stripper and the primary reflux condenser or condensers will be referred to as a first stripper off gas (SOG) stream. For example, the primary reflux condenser could be arranged to partly condense the polluted stream of SOGs from the primary stripper such that a vapour stream of highly volatile substances including methanol is withdrawn from the upper part of the reflux condenser and guided further to the SOG condenser while a liquid fraction comprising less volatile substances is withdrawn from the lower part of the reflux condenser to provide a reflux stream to the stripper. In the SOG condenser, the major portion of the stream including methanol is condensed to be used as a first methanol-containing condensate in the further steps of the methanol producing process while a smaller fraction of highly volatile substances such as non-condensable gases can be transferred away from the system or possibly treated and purified from pollutants. Also, the system comprises at least one first acidification unit arranged to acidify the first methanol-containing condensate in one or more stages with an acid, preferably sulfuric acid. The system further comprises a secondary stripper arranged to strip the acidified first methanol-containing condensate in order to remove pollutants together with the SOGs from the secondary stripper and to obtain a second methanol-containing condensate as the remaining condensate in the second stripper. Furthermore, the system comprises a distillation column arranged to distil the second methanol-containing condensate from the second stripper in a distillation column so as to obtain purified methanol.

According to a second aspect of embodiments herein, the objective is achieved by a method performed in a system for obtaining methanol from foul condensate of a pulping process. The method comprises the step of stripping the foul condensate from pollutants in a primary stripper and primary reflux condenser, whereby a first methanol-containing condensate is obtained by condensing the polluted stripper off gases (SOGs) from the primary stripper passing through the primary reflux condenser by the use of one or several SOG condensers. Also, the method comprises the step of acidifying the first methanol-containing condensate from the SOG condenser in one or more stages. The acidification is performed by adding acid to the first methanol containing condensate in a first acidification unit before the first methanol condensate is guided to a secondary stripper. The method further comprises the step of stripping the acidified first methanol-containing condensate from pollutants in the secondary stripper in order to remove the pollutants together with a second stream of stripper off gases (SOG) and to obtain a second methanol-containing condensate as the remaining condensate from the second stripper. Furthermore, the method comprises the step of distilling the second methanol-containing condensate from the second stripper in a distillation column so as to obtain purified methanol.

By performing a second stripping of the first acidified methanol-containing condensate, a large part of the pollutants, such as, e.g. organic nitrogenous compounds, reduced sulphurous compounds, turpentine, etc. will be stripped off. The acidic condition will contribute to make the pollutants more volatile. For example, pollutants such as hydrogen sulphide and methyl mercaptan are much more volatile at an acidic condition. Other non-polar components such as turpentine and organic sulphides, which often have a high boiling point, will also have an increased volatility at an increased ionic strength. By adding the acid to the first methanol-containing condensate before the condensate is guided to the secondary stripper the concentration of acid and pH-level may be controlled to a desired level and the desired reactions may start in the acidification unit before the condensate is introduced into the secondary stripper. The second stripping will lead to a minor amount of methanol vaporizing which will mix with volatile pollutants so as to form a SOG stream of polluted by-products from the second stripper and a major amount of further purified methanol will remain in the second methanol-containing condensate. Hence, the remaining second methanol-containing condensate will comprise much less pollutants than what previously has been achieved. This highly purified second methanol-containing condensate can then be distilled to remove the water phase comprising the ammonium sulphate and thus obtain an increasingly purified methanol. Hence, the purification of methanol from foul condensate of a pulping process is improved.

Further possible features and benefits of this solution will become apparent from the detailed description below.

BRIEF DESCRIPTION OF THE DRAWINGS

Embodiments will now be described in more detail in relation to the enclosed drawings, in which.

DETAILED DESCRIPTION

The figures herein are schematic and simplified for clarity, and they merely show details which are essential to the understanding of the embodiments presented herein, while other details have been left out.

It should also be noted that the embodiments of the system 200, 300, 400, 500 shown below in FIGS. 2-5 describe non-limiting examples and that the differing features or parts of the embodiments of the system 200, 300, 400, 500 may be considered as independent embodiments or may be considered in any combination with each other, thus forming further combined embodiments which have not been illustrated further for the sake of clarity.

Figure 2:
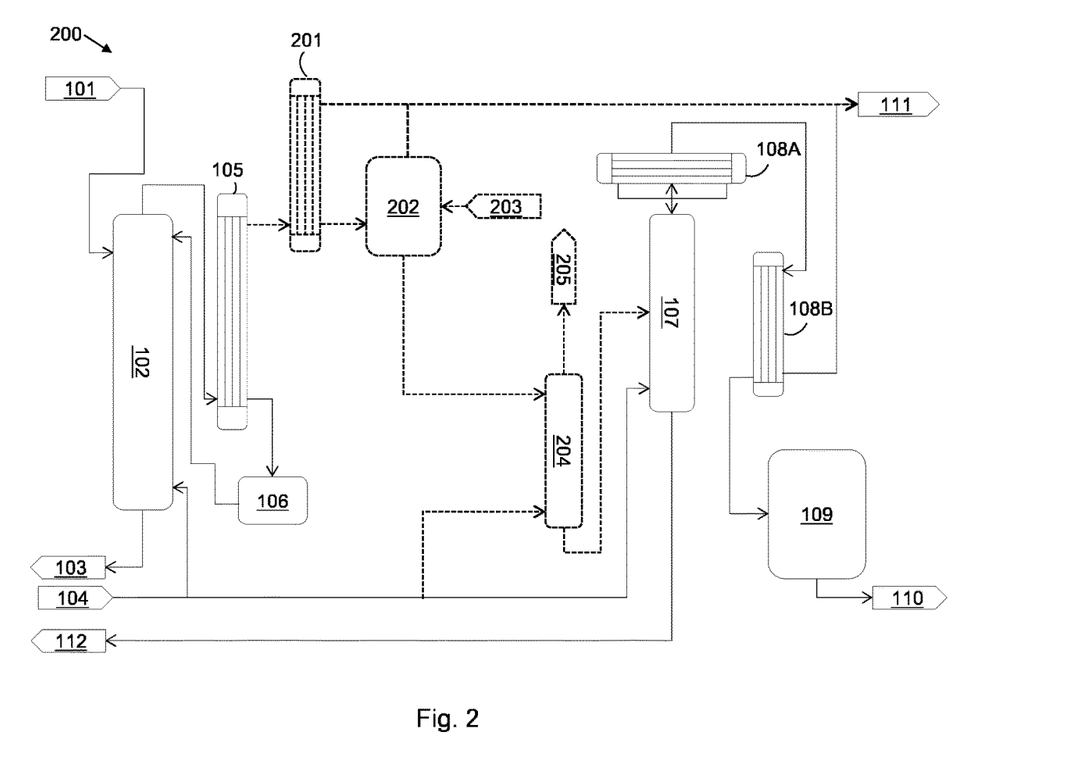
FIGS. 2-5 are schematic illustrations depicting embodiments of a system for obtaining methanol from foul condensate of a pulping process.

FIG. 1 depicts embodiments of a system 100 for obtaining methanol from foul condensate 101 of a pulping process. Here, it should be noted that the system 200 may be similar or identical to the system 100 according to the prior art shown in FIG. 1, except in that it comprises further features and parts. These further features and parts of the embodiments are indicated in FIG. 2 by the dashed lines. The similar features or parts of the system 100 according to the prior art shown in FIG. 1 and the embodiments of system 200 are indicated by being denoted with the same reference numerals.

For example, the system 200 comprises a primary stripper 102. The primary stripper 102 being arranged to strip the foul condensate 101 from pollutants, whereby a first methanol-containing condensate is obtained by condensing a first stream of stripper off gases (SOGs) from the primary stripper 102 in a primary SOG condenser 201. The primary stripper 102 usually comprises a primary reflux condenser 105, or heat exchanger, arranged to partly condense the polluted SOGs from the primary stripper 102 so as to provide a reflux stream to the primary stripper 102. The first stream of SOGs may thus stream via the primary reflux condenser 105, if such a condenser is present in the system, before being guided to the primary SOG condenser to obtain the first methanol-containing condensate. One or more additional primary SOG condensers 201 can be used to condense the first stream of SOGs so as to obtain the first methanol-containing condensate from the polluted SOGs. Hence, it is the condensate derived from the first stream of SOGs produced in the primary stripper 102 and condensed in the SOG condenser 201 which will be the first methanol containing condensate used as basis for production of a further methanol enriched and purified product in the following steps.

The system 200 also comprises a first acidification unit 202. The first acidification unit 202 is arranged to acidify the first methanol-containing condensate. This can be performed by adding acid 203, such as, e.g. sulfuric acid, $H_2SO_4$, to the first methanol-containing condensate obtained from the at least one primary SOG condenser 201. By adding acid, preferably sulfuric acid, to the first methanol-containing condensate, the nitrogenous compounds, mainly in the form of ammonium, in the first methanol-containing condensate will be bound forming ammonium sulphate. This means that later upon vaporizing in the distillation column 107, the methanol will be transferred to the vapour phase while the ammonium sulphate will be retained in the remaining liquid phase stream 112. However, it should be noted that other nitrogenous compounds, primarily organic, and the sulphurous compounds may not be retained in the liquid phase in the same way. Although, by adding acid, the level of ions in the first methanol-containing condensate will increase, which in turn will increase the volatility of the different pollutants, such as, e.g. organic nitrogenous compounds, reduced sulphurous compounds, turpentine, etc., dissolved in the acidified first condensate. The turpentine and other hydrocarbon on the other hand may be separated from the first methanol-containing condensate by decanting, as described further below.

Furthermore, the system 200 further comprises a secondary stripper 204. The secondary stripper 204 is arranged to strip the acidified first methanol-containing condensate from pollutants and obtain a second methanol-containing condensate. In other words, the secondary stripper 204 is arranged to strip the acidified first methanol-containing condensate in order to remove the pollutants together with a second stream of SOGs 205 from the secondary stripper 204. This is performed in the secondary stripper 204, e.g. by water vapour 104 being introduced at the bottom of the secondary stripper 204. Due to the increased acidity and level of ions in the first methanol-containing condensate, the increased volatility of some of the pollutants, such as organic nitrogenous compounds, reduced sulphurous compounds, turpentine etc., will enable an increased part of the pollutants in the first methanol-containing condensate to be removed with the second stream of SOGs 205.

The second methanol-containing condensate is obtained as the remaining condensate in the secondary stripper 204. The second methanol-containing condensate is then transferred to the distillation column 107. According to the embodiments herein, the distillation column 107 is arranged to distil the second methanol-containing condensate from the secondary stripper 204 so as to obtain a methanol. The distilled methanol from the distillation column 107 can then be condensed via the distiller reflux condenser 108A and the distiller final condenser 108B. The methanol from the distiller final condenser 108B can then be collected in the methanol tank 109 from which the methanol 110 may be extracted.

Hence, in the secondary stripper 204, it is the condensate from the secondary stripper which forms a main flow which will be basis for production of a further methanol enriched product in the following steps while there is a minor flow of pollutants, by-products and some methanol removed as the second stream of SOG 205. This is in contrast to the primary stripper 102 wherein it is the first stream of SOG which is condensed in the primary SOG condenser 201 and used as the product flow containing the main portion of methanol while a liquid fraction of purified condensate 103 is removed from the process.

It should be noted that the second methanol-containing condensate obtained in the secondary stripper 204 will comprise substantially less amounts of pollutants, e.g. organic nitrogenous compounds, reduced sulphurous compounds, turpentine etc., than the first methanol-containing condensate. This means that distilled methanol obtained from the distillation column 107 in the system 200 will have a significantly higher degree of purification than, for example, the distilled methanol of the system 100 in FIG. 1 according to the prior art. Hence, the system 200 will provide an improved purification of methanol from foul condensate of a pulping process.

Figure 3:
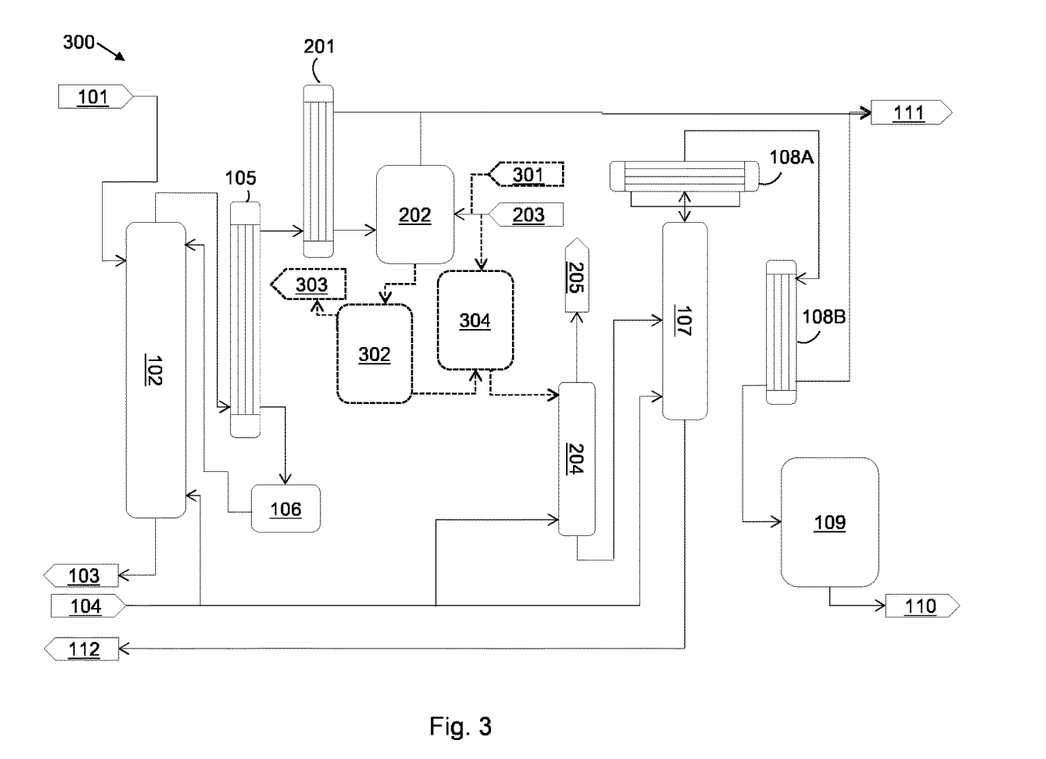

FIG. 3 depicts embodiments of a system 300 for obtaining methanol from foul condensate 101 of a pulping process. Here, it should be noted that the embodiments of the system 300 may be similar or identical to the system 200 according to the embodiments described with reference to FIG. 2, except in that it comprises further features and parts. These further features or parts of the embodiments are indicated in FIG. 3 by the dashed lines. The similar features or parts of the embodiments of system 300 and the embodiments of system 200 are indicated by being denoted with the same reference numerals.

In some embodiments, the system 300 may comprise a first adding unit 301. The first adding unit 301 may be arranged to add sulphite ions to the acidified first methanol-containing condensate. The sulphite ions may, for example, be provided in the form of sodium bisulphite, $NaHSO_3$. This may be performed so as to facilitate the separation of turpentine, or other hydrocarbons forming their own phase, from the acidified first methanol-containing condensate. This advantageously also creates a buffer in the first acidified methanol-containing condensate which simplifies and eases the control of the pH-level when, for example, providing amounts of acid 203 into the first methanol-containing condensate by the first acidification unit 202 and/or second acidification unit 304 (see FIG. 3 below). This is because during the acidification of the first methanol-containing condensate, there is a risk that the pH-level reaches low levels, such as, e.g. <pH 5, i.e. below pH 5, and, at those low pH-levels, there is a risk of polymerization of the turpentine in the first methanol-containing condensate. This polymerization may create a sticky phase which may cause severe clogging.

To further avoid or reduce the risk of polymerization, the system 300 can comprise a first decanter 302. The first decanter 302 may be arranged to decant the first methanol-containing condensate. This may be performed so as to separate turpentine 303, or other hydrocarbons forming their own phase, from the first methanol-containing condensate. Hence, the at least one first decanter 302 will also allow some of the turpentine 303 to be extracted from the first methanol-containing condensate. Furthermore, since the decanting of the first methanol-containing condensate by the first decanter 302 is improved by high levels of ions, performing at least some of the acidification in the first acidification unit 202 and adding of sulphite ions in the first adding unit 301 before the decantation may be advantageous in order to separate more of the turpentine from the first methanol-containing condensate.

Further, according to some embodiments, the system 300 can also comprise a second acidification unit 304. The second acidification unit 304 can be arranged to acidify the decanted first methanol-containing condensate from the first decanter 302. This means that the acidification of the first methanol-containing condensate may be performed in one or more stages before and/or after the decantation in the first decanter 302. In this case, a first stage may be adding a first amount of acid 203 in the first acidification unit 202 before the decantation in the first decanter 302. Here, the first amount of acid 203 may be selected in order to avoid or reduce polymerization of the turpentine 303 in the first methanol-containing condensate in view of the pH-level. After that, a second stage may be adding a second amount of acid 203 in the second acidification unit 304 after the decantation in the first decanter 302. Since some of the turpentine 303 has been extracted and lowered the risk of polymerization, the second amount of acid 203 may be chosen taken this into consideration.

From the above it should also be noted that, according to some embodiments, the decanting of the first methanol-containing condensate may also be performed before the acidification and/or the adding of sulphite ions. In other words, in some embodiments, the decanting may be performed in one or more stages before, in between, and/or after the one or more stages of acidification and/or adding of sulphite ions in the system 300.

Figure 4:
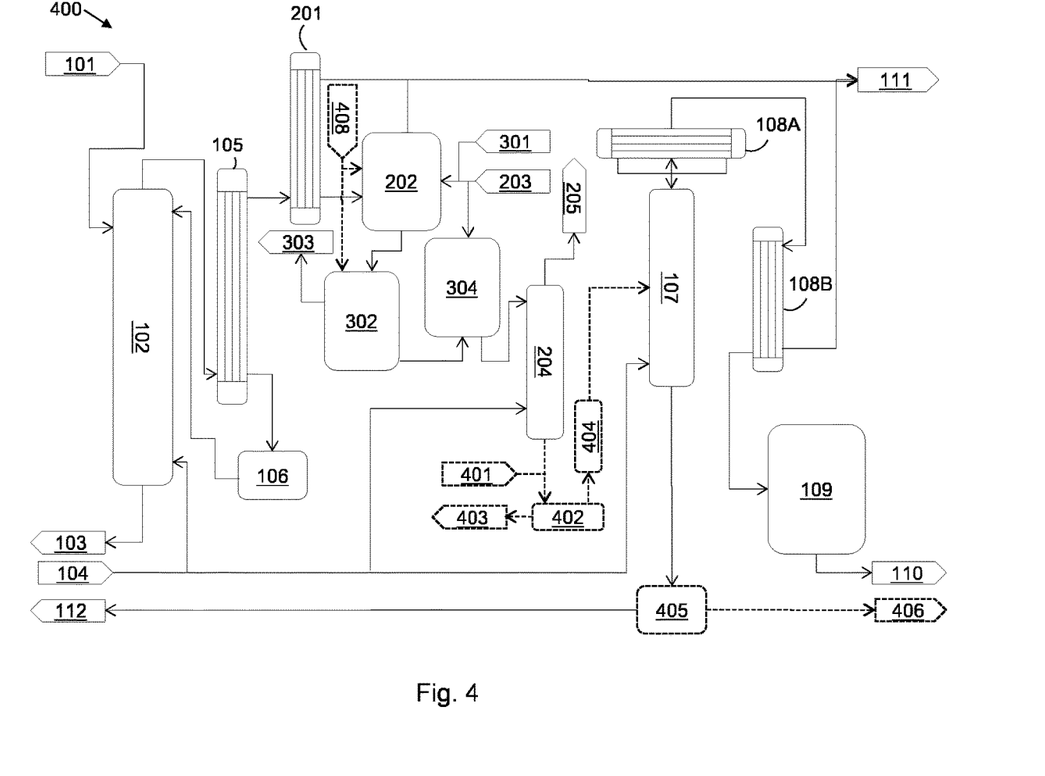

FIG. 4 depicts embodiments of a system 400 for obtaining methanol from foul condensate 101 of a pulping process. Here, it should be noted that the embodiments of the system 400 may be similar or identical to the system 200, 300 according to the embodiments described with reference to FIGS. 2-3, except in that it comprises further features and parts. These further features or parts of the embodiments are indicated in FIG. 4 by the dashed lines. The similar features or parts of the embodiments of system 400 and the embodiments of system 200, 300 are indicated by being denoted with the same reference numerals.

In some embodiments, the system 400 may comprise an oxidation adding unit 401. The oxidation adding unit 401 may be arranged to add an oxidation agent in order to oxidize the second methanol-containing condensate from the secondary stripper 204 prior to distilling the second methanol-containing condensate in the distillation column 107. By adding an oxidant, i.e. a chemical compound such as hydrogen peroxide ($H_2O_2$) or chlorine dioxide ($ClO_2$) that will cause oxidation of other compounds, the oxidation adding unit 401 may advantageously increase the degree of purification of the second methanol-containing condensate in reference to the sulphurous compounds in the second methanol-containing condensate. This is because the oxidation in the oxidation adding unit 401 will cause oxidation of the sulphurous compounds in the second methanol-containing condensate. This means that the sulphurous compounds in the second methanol-containing condensate will become less volatile, and also odourless. This, in turn, means that the oxidized sulphurous compounds in the second methanol-containing condensate to a large extent will remain in the water phase 112, in the distillation column 107 instead of being transferred away with the distilled methanol out of the distillation column 107.

In some embodiments, the system 400 may also comprise a second decanter 402. The second decanter 402 may be arranged to decant the second methanol-containing condensate from the secondary stripper 204 prior to distilling the second methanol-containing condensate in the distillation column 107. This may be performed so as to separate some of the remaining hydrocarbons 403, such as turpentine, forming their own phase, from the second methanol-containing condensate if needed.

Furthermore, according to some embodiments, the system 400 may also comprise a third acidification unit 404. The third acidification unit 404 may be arranged to acidify the second methanol-containing condensate from the secondary stripper 204 prior to distilling the second methanol-containing condensate in the distillation column 107. Since the second methanol-containing condensate from the secondary stripper 204, or the decanted second methanol-containing condensate from the second decanter 402, may comprise relatively low amounts of turpentine, or other hydrocarbons forming their own phase, it may be advantageous to perform the final acidification before the distilling, e.g. in this third acidification unit 404. This is because an excess of acid may here be added in order to ensure that substantially all of the ammonium is retained in the water phase during the distillation in the distillation column 107 instead of being transferred away with the distilled methanol out of the distillation column 107.

Although the oxidation, decanting and acidification of the second methanol-containing condensate from the secondary stripper 204 may be performed in no particular order, it should also be noted that it may also be particularly advantageous to perform the oxidation in the oxidation unit 401 prior to the acidification in the third acidification unit 404. This is because the oxidation in the oxidation unit 401 will prevent or reduce the risk of polymerization of the turpentine in the second methanol-containing condensate, when acidifying the second methanol-containing condensate down to low pH-levels (e.g. <pH 5) in the third acidification unit 404. Also, the oxidation will further help to reduce the pH-level of the second methanol-containing condensate even further (e.g. <pH 4).

In some embodiments, the system 400 may further comprise a third decanter 405. The third decanter 405 may be arranged to decant the remaining condensate from the distillation column 107. This may be performed so as to separate some of the remaining turpentine, or other hydrocarbons forming their own phase, from the water phase of second methanol-containing condensate remaining after the distillation in the distillation column 107. Hence, the third decanter 405 will also allow some of the hydrocarbons 406, such as turpentine, forming their own phase to be extracted from the from the water phase of the condensate from the distillation column 107, while the remaining water phase 112 may be transferred away to, for example, a waste water treatment facility. A waste water treatment facility is typically found at a pulp processing mill. This is also advantageous as said water phase comprise ammonium sulphate, which contributes as nutrients for microbes.

In some embodiments, the system 400 may further comprise a second adding unit 408. The second adding unit 408 may be arranged to add turpentine, or other hydrocarbons, to first methanol-containing condensate when the amount of turpentine, or other hydrocarbons, in the first methanol-containing condensate is below a determined threshold level. This may advantageous in order to further extract sulphurous components in the first methanol-containing condensate, when the turpentine is insufficient for a satisfying extraction. The turpentine, or other hydrocarbons, may be added to the first methanol-containing condensate at different stages.

Figure 5:
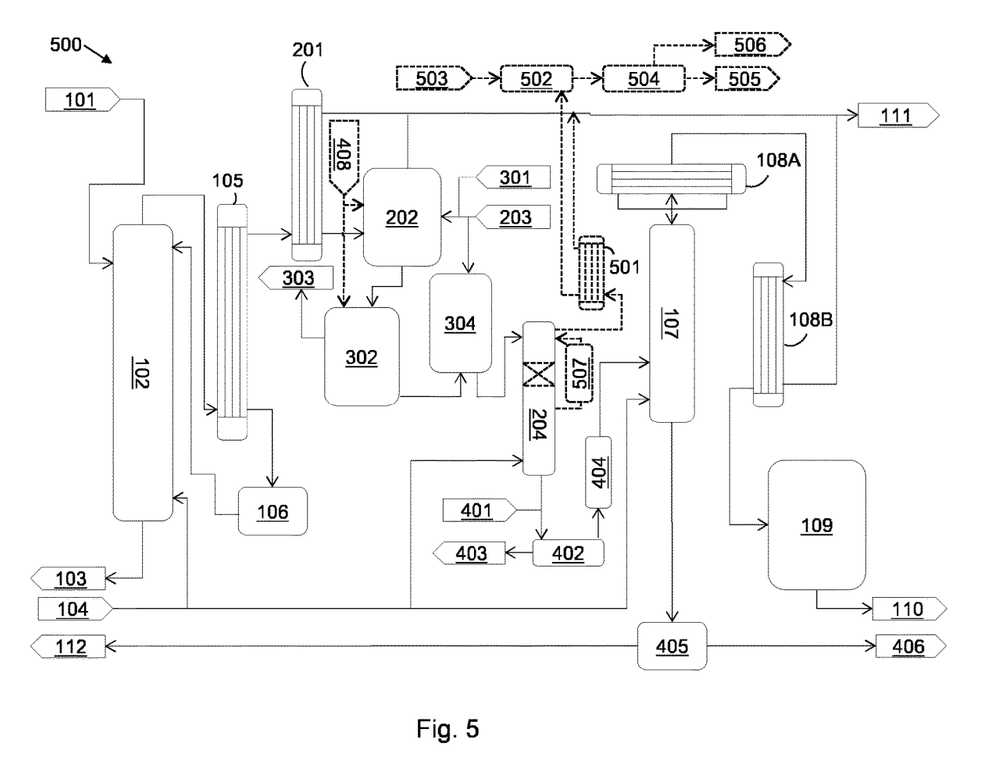

FIG. 5 depicts embodiments of a system 500 for obtaining methanol from foul condensate 101 of a pulping process. Here, it should be noted that the embodiments of the system 500 may be similar or identical to the system 200, 300, 400 according to the embodiments described with reference to FIGS. 2-4, except in that it comprises further features and parts. These further features or parts of the embodiments are indicated in FIG. 5 by the dashed lines. The similar features or parts of the embodiments of system 500 and the embodiments of system 200, 300, 400 are indicated by being denoted with the same reference numerals.

In some embodiments, the system 500 may also comprise at least one secondary SOG condenser 501. The at least one secondary SOG condenser 501 is arranged to condense the SOGs from the secondary stripper 204 comprising the pollutants into a polluted condensate. The SOGs from the secondary stripper 204 may also be referred to as a second stripper off gas stream. In some cases, the polluted condensate may, for example, be transferred away for destruction, e.g. to be burned together with the black liquor after the evaporation stage in a soda recovery boiler. However, this means that the methanol remaining in the polluted condensate will be lost.

An alternative way of handling the polluted condensate according to some embodiments herein is to transfer the polluted condensate to an extraction unit 502 that may be comprised in the system 500. The extraction unit 502 may be arranged to extract pollutants in the polluted condensate by mixing the polluted condensate with turpentine 503. Advantageously, the turpentine 503 used may here be turpentine extracted within the system 500, such as, e.g. turpentine 303 extracted from the first decanter 302, turpentine 403 extracted from the second decanter 402, and/or turpentine 406 extracted from the third decanter 405. However, preferably, the turpentine 303 extracted from the first decanter 302 should be used as it is most likely to be the large and less polluted extracted turpentine. In this case, the system 500 may further comprise a fourth decanter 504. The fourth decanter 504 may be arranged to decant the remaining polluted condensate and turpentine mixture, so as to separate turpentine 505 from the polluted condensate and turpentine mixture. This will be advantageously as the turpentine, or any other non-polar extraction medium for that matter, will extract other non-polar components, such as, e.g. organic sulphides, organic nitrogen compounds, etc., from the methanol 506 in the remaining polluted condensate and turpentine mixture, thereby reducing the pollutants in the remaining methanol 506. This enables the methanol 506 in the polluted condensate from the secondary SOG condenser 501 to be extracted and used. For example, the methanol 506 may be added back into the system 500, for example, to the first methanol-containing condensate. Also, as shown in FIG. 5, the non-condensable gases 111 of the secondary SOG condenser 501 transferred away from the system 500.

Furthermore, in some embodiments, the system 500 may comprise a cooling arrangement 507. The cooling arrangement 507 may be arranged to cool the acidified first methanol-containing condensate at the upper-most equilibrium stage of the secondary stripper 204. In controlling and optimizing the operation of the secondary stripper 204, the supply of water vapour, i.e. the water vapour or steam feed, within the secondary stripper 204 may be controlled, i.e. decreased, maintained or increased. A high water vapour feed through the secondary stripper 204 will lead to a high vapour flow out of the top of the secondary stripper 204. If the latter is too high, then this may cause too much of the methanol to be transferred away together with the SOGs of the secondary stripper 204. Hence, by cooling the acidified first methanol-containing condensate in the upper-most equilibrium stage of the secondary stripper 204, the vapour flow may at least partly be condensed and thus remain in the secondary stripper 204, which ensures that not too much methanol is transferred away together with the SOGs to, for example, the secondary SOG condenser 501. Therefore, it should be noted that the pollutant removal efficiency of the secondary stripper 204 is strongly depended on the ratio of flows of vapour and the second methanol-containing condensate in the secondary stripper.

According to one example, the cooling arrangement 507 may be arranged to extract some of the condensed second methanol-containing condensate from a lower equilibrium stage of the secondary stripper 204, cool the extracted second methanol-containing condensate e.g. in a separate cooler, and then return the cooled-off second methanol-containing condensate to the secondary stripper 204 again at the upper equilibrium stage. However, it should also be noted that other ways of cooling the first methanol-containing condensate in an upper equilibrium stage may also be envisioned, such as, for example, extending pipes into the secondary stripper 204 with cooling liquid inside, having a cooling coil at the upper-most equilibrium stage of the secondary stripper 204, or by sub-cooling the condensate feed of the secondary stripper 204.

In the systems 200, 300, 400, 500 in FIGS. 2 to 5, there is disclosed the use of a separate primary reflux condenser 105. However, such a reflux condenser could form part of the primary stripper 102. Furthermore, it is disclosed a single primary SOG condenser but there could be several such condensers present instead of only one primary SOG condenser.

Figure 6:
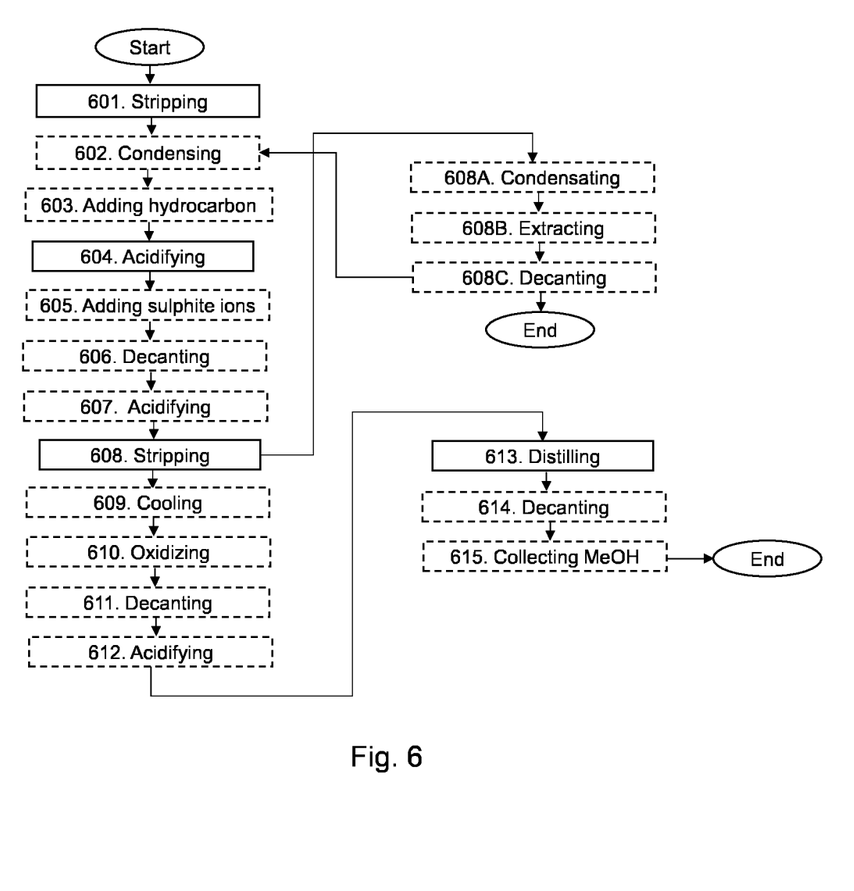
FIG. 6 is a flow chart of embodiments of a method for obtaining methanol from foul condensate of a pulping process.

Example of embodiments of a method performed in a system 200, 300, 400, 500, for obtaining methanol from foul condensate 101 of a pulping process will now be described with reference to the flowchart depicted in FIG. 6. FIG. 6 is an illustrated example of actions or operations which may be performed in the embodiments of the system 200, 300, 400, 500.

Action 601. The system 200, 300, 400, 500 strips the foul condensate 101 from pollutants in a primary stripper 102, whereby a first methanol-containing vapour is obtained from the primary stripper 102.

Action 602. The system 200, 300, 400, 500 condenses the polluted stripper off gases (SOGs) of the primary stripper 102 to obtain the first methanol-containing condensate.

Action 603. As an option, in some embodiments, the system 200, 300, 400, 500, may add turpentine, or other hydrocarbons, to the first methanol-containing condensate when the amount of turpentine, or other hydrocarbons, in the first methanol-containing condensate is below a determined threshold level.

Action 604. The system 200, 300, 400, 500 acidifies the first methanol-containing condensate. The acidification may for example be performed by adding acid 203 to the first methanol containing condensate in a first acidification unit 202.

Action 605. After the acidification of the first condensate in Action 604, the system 200, 300, 400, 500 may add sulphite ions to the acidified first methanol-containing condensate.

Action 606. After the adding of the sulphite ions in Action 605, the system 200, 300, 400, 500 may decant the first methanol-containing condensate.

Action 607. After the decanting of the first condensate in Action 606, the system 200, 300, 400, 500 may acidify the decanted first methanol-containing condensate.

Action 608. The system 200, 300, 400, 500 strips the acidified first methanol-containing condensate from pollutants in a secondary stripper 204 to obtain a second methanol-containing condensate.

Action 608A. After the stripping in Action 608, the system 200, 300, 400, 500 may condense the second stream of SOGs comprising the pollutants from the secondary stripper 204 into a polluted condensate.

Action 608B. After the condensing in Action 608A, the system 200, 300, 400, 500 may extract at least part of the pollutants in the polluted condensate by mixing the polluted condensate with turpentine.

Action 608C. After the extraction in Action 608B, the system 200, 300, 400, 500 may decant the remaining polluted condensate and turpentine mixture, so as to separate turpentine from the polluted condensate and turpentine mixture. Here, it should be noted that the remaining methanol may be added back into the system 200, 300, 400, 500, for example, to the first methanol-containing condensate in Action 602.

Action 609. In the stripping in Action 607, the system 200, 300, 400, 500 may also cool the acidified first methanol-containing condensate in an upper-most equilibrium stage of the secondary stripper 204.

Action 610. After the stripping in Action 608 or cooling in Action 609, the system 200, 300, 400, 500 may oxidize the second methanol-containing condensate.

Action 611. After the oxidation in Action 610, the system 200, 300, 400, 500 may decant the second condensate.

Action 612. After the decantation in Action 611, the system 200, 300, 400, 500 may acidify the second methanol-containing condensate.

Action 613. The system 200, 300, 400, 500 distils the second methanol-containing condensate from the secondary stripper 204 in a distillation column 107 so as to obtain methanol.

Action 614. After the distilling in Action 613, the system 200, 300, 400, 500 may decant the remaining methanol-containing condensate.

Action 615. Finally, the system 200, 300, 400, 500 may obtain the methanol from the distillation column 107.

Here, it should be noted that the acidification in Action 604 and 607 may, according to some embodiments, be performed in one or more stages after the stripping in Action 601, after the decantation in Action 606, or after the stripping in Action 608, or in any combination thereof. It should also be noted that the decantation in Action 606 may be performed in one or more stages after the stripping in Action 601, or after or in between one of the acidification stages described in Action 604 and 607, or in any combination thereof.

The terminology used in the detailed description of the particular embodiments illustrated in the accompanying drawings is not intended to be limiting of the described system or method therein. As used herein, the term "and/or" comprises any and all combinations of one or more of the associated listed items. Further, as used herein, the common abbreviation "e.g.", which derives from the Latin phrase "exempli gratia," may be used to introduce or specify a general example or examples of a previously mentioned item, and is not intended to be limiting of such item. If used herein, the common abbreviation "i.e.", which derives from the Latin phrase "id est," may be used to specify a particular item from a more general recitation. The common abbreviation "etc.", which derives from the Latin expression "et cetera" meaning "and other things" or "and so on" may have been used herein to indicate that further features, similar to the ones that have just been enumerated, exist.

As used herein, the singular forms "a", "an" and "the" are intended to comprise also the plural forms as well, unless expressly stated otherwise. It will be further understood that the terms "includes," "comprises," "including" and/or "comprising," when used in this specification, specify the presence of stated features, actions, integers, steps, operations, elements, and/or components, but do not preclude the presence or addition of one or more other features, actions, integers, steps, operations, elements, components, and/or groups thereof.

Unless otherwise defined, all terms comprising technical and scientific terms used herein have the same meaning as commonly understood by one of ordinary skill in the art to which the described embodiments belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The embodiments herein are not limited to the above described preferred embodiments. Various alternatives, modifications and equivalents may be used. Therefore, the above embodiments should not be construed as limiting.

The invention claimed is:

1. A method performed in a system for obtaining a methanol from a foul condensate of a pulping process, the method comprising:
   stripping the foul condensate from first pollutants in a primary stripper to produce polluted stripper off gases (SOGs), whereby a first methanol-containing condensate is obtained from the polluted SOGs of the primary stripper by condensing the polluted SOGs of the primary stripper to obtain the first methanol-containing condensate;
   acidifying the first methanol-containing condensate in a first acidification unit to produce an acidified first methanol-containing condensate where after the acidified first methanol-containing condensate is guided further to a secondary stripper;
   stripping the acidified first methanol-containing condensate from second pollutants in the secondary stripper in order to remove the second pollutants together with second SOGs and to obtain a second methanol-containing condensate as a remaining condensate in the secondary stripper; and
   distilling the second methanol-containing condensate from the secondary stripper in a distillation column so as to obtain the methanol and a remaining methanol-containing condensate.

2. The method according to claim 1, further comprising adding sulphite ions to the acidified first methanol-containing condensate.

3. The method according to claim 1, further comprising decanting the first methanol-containing condensate to obtain a decanted first methanol-containing condensate.

4. The method according to claim 3, further comprising acidifying the decanted first methanol-containing condensate.

5. The method according to claim 1, further comprising oxidizing the second methanol-containing condensate.

6. The method according to claim 1, further comprising decanting the second methanol-containing condensate.

7. The method according to claim 1, further comprising acidifying the second methanol-containing condensate.

8. The method according to claim 1, further comprising decanting the remaining methanol-containing condensate after the distilling.

9. The method according to claim 1, further comprising adding an amount of turpentine, or other hydrocarbons, to the first methanol-containing condensate when the amount of turpentine, or other hydrocarbons, in the first methanol-containing condensate is below a determined threshold level.

10. The method according to claim 1, further comprising condensing the second SOGs comprising the second pollutants from the secondary stripper into a polluted condensate;

extracting at least part of the second pollutants in the polluted condensate by mixing the polluted condensate with turpentine to obtain a remaining polluted condensate and turpentine mixture; and decanting the remaining polluted condensate and turpentine mixture, so as to separate turpentine from the remaining polluted condensate and turpentine mixture.

11. The method according to claim 1, further comprising cooling the acidified first methanol-containing condensate in an upper equilibrium stage of the secondary stripper.

\* \* \* \* \*